US00PP26597P2

(12) United States Plant Patent
Gabriel

(10) Patent No.: US PP26,597 P2
(45) Date of Patent: Apr. 12, 2016

(54) BLUEBERRY PLANT NAMED 'OBF0627'

(50) Latin Name: *Vaccinium corymbosum*
Varietal Denomination: OBF0627

(71) Applicant: Robert Gabriel, Silverton, OR (US)

(72) Inventor: Robert Gabriel, Silverton, OR (US)

( * ) Notice: Subject to any disclaimer, the term of this patent is extended or adjusted under 35 U.S.C. 154(b) by 190 days.

(21) Appl. No.: 13/998,287

(22) Filed: Oct. 17, 2013

(51) Int. Cl.
*A01H 5/08* (2006.01)

(52) U.S. Cl.
USPC ..... Plt./157

(58) Field of Classification Search
USPC ..... Plt./157
See application file for complete search history.

(56) References Cited

PUBLICATIONS

Upov International Union for the Protection of New Varieties of Plants 2012, retrieved on Jul. 16, 2015, retrieved from the Internet at <http://www.upov.int/edocs/infdocs/en/upov_inf_12_4.pdf> pp. 1 and 4.*

* cited by examiner

*Primary Examiner* — June Hwu
(74) *Attorney, Agent, or Firm* — Klarquist Sparkman, LLP

(57) ABSTRACT

A new and distinct cultivar of Northern Highbush Blueberry plant characterized by its extremely firm fruit and the concentrated ripening of its berries. It an excellent berry for mechanical harvest and the extra firm berries give it a long shelf life. In addition the new cultivar produces mid to late-season, has a medium sweet, floral flavor, small, dry stem scars, an upright moderately spreading habit, and excellent vigor.

3 Drawing Sheets

Botanical classification: *Vaccinium corymbosum.*
Variety nomination: 'OBF0627'.

FIELD

The present invention relates to a new and distinct cultivar of Northern Highbush blueberry, or *Vaccinium corymbosum* and given the name 'OBF0627'. *Vaccinium corymbosum* is of the family Ericaceae.

BACKGROUND

Northern Highbush blueberries are the most commonly planted blueberries used for commercial and home production of fruit in the Northern U.S. and Canada. The new cultivar is from a planned breeding program for an improved blueberry. It was developed at a blueberry farm in Silverton, Oreg. using open pollination with unnamed seedlings for the parents.

This new Northern Highbush Blueberry is uniquely distinguished by its extremely firm fruit and the concentrated ripening of its berries. It is an excellent berry for mechanical harvest and the extra firm berries give a long shelf life. In addition the new cultivar produces mid to late-season, has a medium sweet, floral flavor, small, dry stem scars, and has an upright moderately spreading compact habit.

Compared to *Vaccinium corymbosum* 'Draper', U.S. Plant Pat. No. 15,103, the new cultivar has firmer berries, a smaller habit, and a later fruiting season.

Compared to *Vaccinium corymbosem* '06-22', U.S. Plant patent application Ser. No. 13/998,303, the new cultivar has a more spreading habit and a medium sweet, floral berry flavor rather than sweet-tart.

Asexual propagation by stem tip cuttings in Silverton, Oreg., shows that the foregoing characteristics and distinctions come true to form and are established and transmitted through succeeding propagations. The present invention has not been evaluated under all possible environmental conditions. The phenotype may vary with changes in environment without a change in the genotype of the plant.

SUMMARY

The foregoing and other objects, features, and advantages of the invention will become more apparent from the following detailed description, which proceeds with reference to the accompanying figures.

DETAILED DESCRIPTION

Figure 1:
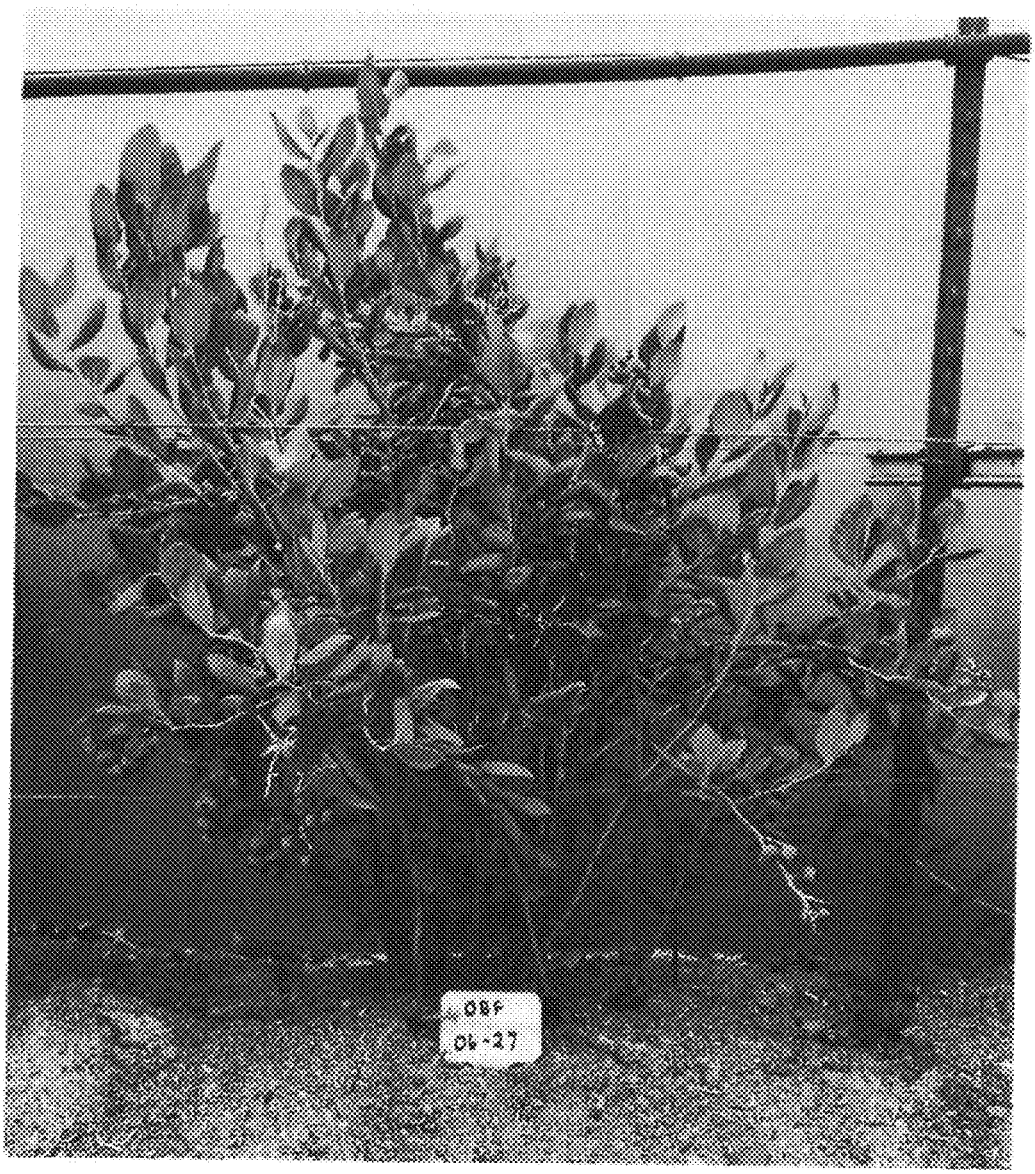
FIG. 1 shows a 3 year old plant of the new cultivar growing in the field in fruit in mid-July in Silverton, Oreg.
Figure 2:
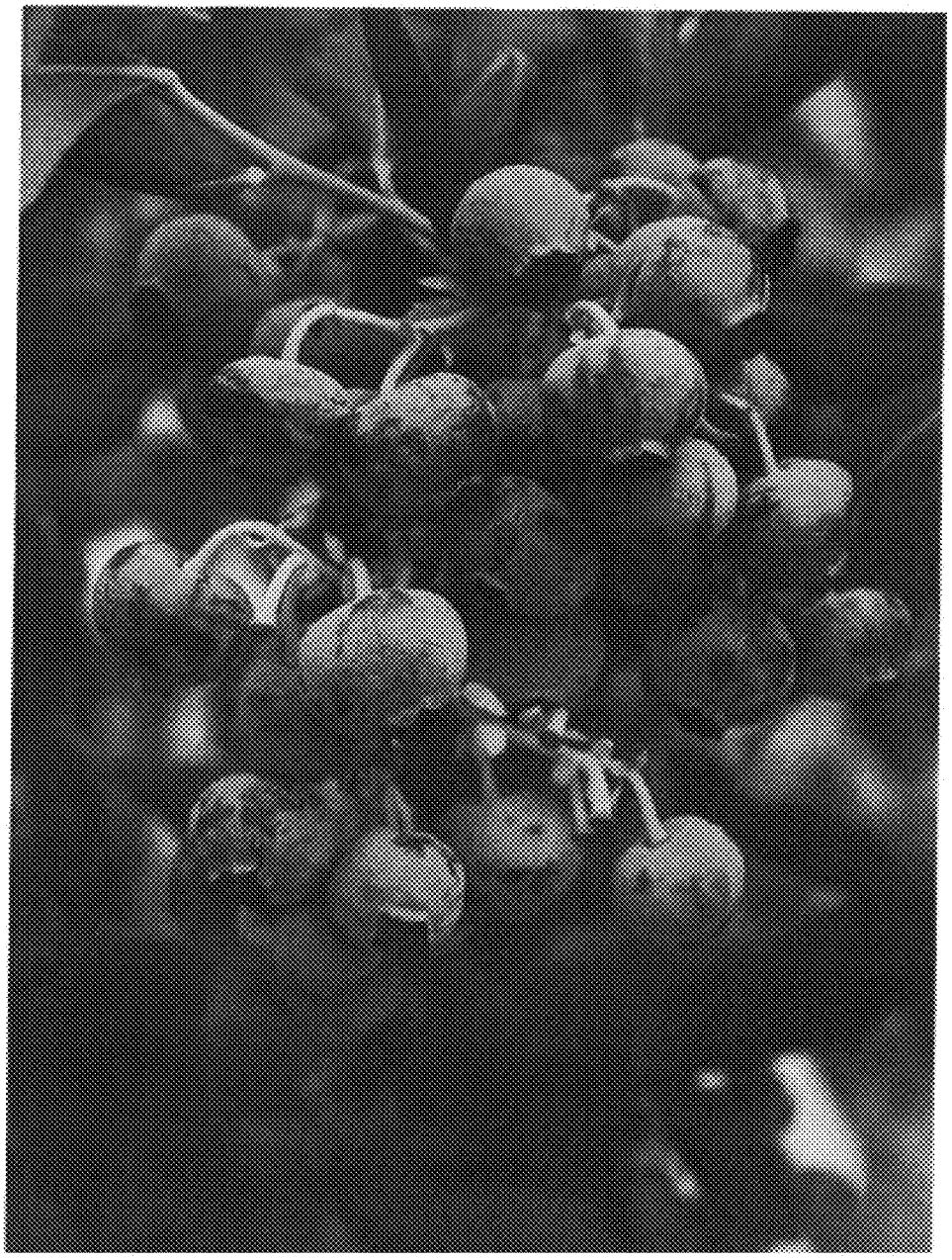
FIG. 2 shows a close up of the fruit clusters of my cultivar.
Figure 3:
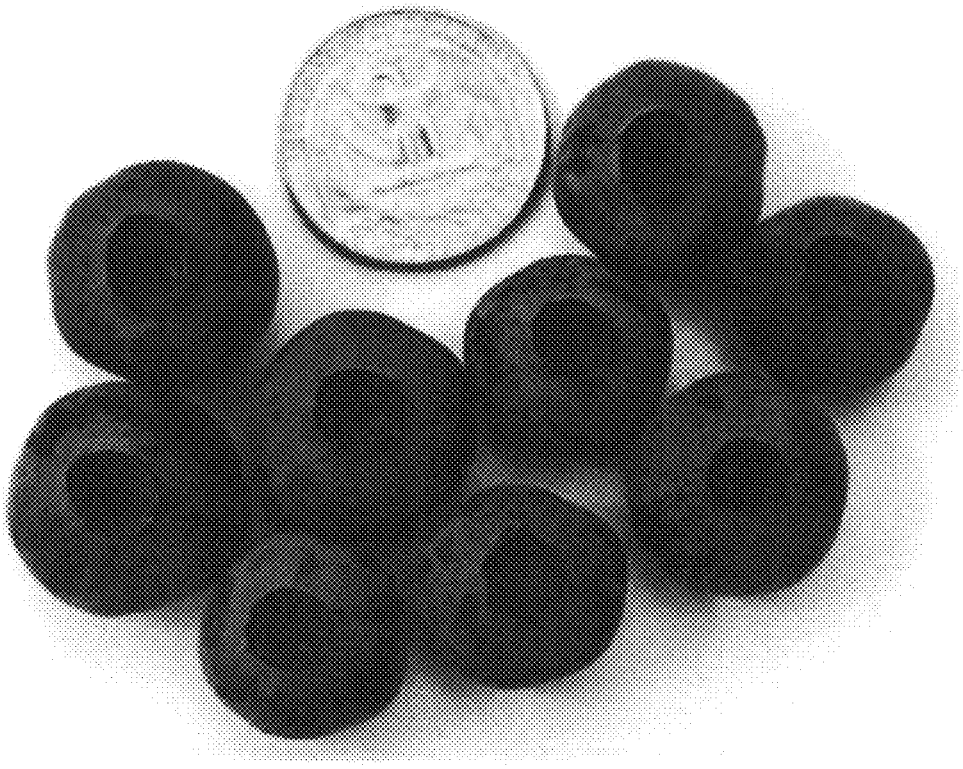
FIG. 3 shows a close up of the berries of my new cultivar compared in size to the size of a US quarter.

The following is a detailed description of the new cultivar based on observations taken in mid-July of a three-year-old specimen grown in the field under average conditions in full sun in Silverton, Oreg. Silverton, Oreg. is in USDA hardiness zone 8. The color descriptions are all based on *The Royal Horticultural Society Colour Chart*, 5$^{th}$ edition.

Plant:

*Type*.—Deciduous shrub.

*Hardiness*.—Not yet determined, observed growing in USDA Zone 8.

*Size*.—About 93 cm tall and 83 cm wide.

*Growth habit*.—Upright, moderately spreading.

*Productivity*.—Medium to high crop yields.
*Chilling requirement*.—Expect 1000 hours.
*Vigor*.—Good.

Stem (cane):
*Type*.—Woody, erect to semi-erect with excellent branching.
*Size*.—Trunk base is 4 cm at 1 cm above the ground, 9 to 10 mm wide at 3 year old, 4 to 5 mm wide at 2 year old, 2 to 4 mm wide at this year growth.
*# Stems*.—4 main stems from the base.
*Internodes*.—1.5 to 2.5 cm long.
*Surface*.—Glabrous.
*Rooting*.—From current season's wood takes 60 to 90 days to root.
*Date of vegetative bud burst at time of culture*.—Second week of March in Silverton, Oreg.
*Color*.—This year's growth — Yellow Green 146D tinted Greyed Red 182B in sun, 1 year old Yellow Green 146D to Brown 200B and 200A where it was tinted last year, 2+ year old — Brown 200B and 200A.

Leaf:
*Type*.—Simple.
*Shape*.—Elliptic.
*Arrangement*.—Alternate.
*Margins*.—Entire.
*Apex*.—Acute.
*Base*.—Cuneate.
*Venation*.—Pinnate, with veins Yellow Green 145C on top and 145D on bottom side.
*Blade size*.—Grows to 5.5 cm long and 3.1 cm wide.
*Surface*.—Glabrous on both sides.
*Petiole description*.—4 mm long and 1.5 mm wide, Yellow Green 145C on top side and tinted Greyed Red 181D on bottom side.
*Leaf color*.—Topside Green 137A, bottom side closest to Greyed Green 191A.

Inflorescence:
*Type*.—Raceme or cluster, within each cluster are usually 5 to 8 groups of about 8 flowers, grouped very close together.
*Dimensions of cluster*.—4 cm wide by 9 to 14 cm long.
*Number of flowers per cluster*.—About 50.
*Peduncle*.—1.5 cm long and 3 mm wide, glabrous, Yellow Green 152A, tinted Greyed Red 181A in sun.
*Pedicel description*.—5 to 7 mm long, 1 mm wide, glabrous, Yellow Green 144A, tinted in sun Greyed Red 181B.
*Bloom period*.—Mid to late April in Silverton, Oreg.

Flower bud:
*Size*.—10 mm long and 7 mm wide.
*Shape*.—Ovoid.
*Color*.—White N155B, tinted Greyed Red 181B.

Flower:
*Type*.—Regular, urceolate.
*Description*.—10 mm long and 9 mm wide overall; with corolla 10 mm long and 9 mm wide, 6 lobes, ovate, reflexed, 2 mm wide and 1 mm deep, entire, tip obtuse, glabrous, color inside and out White 155C to N155B; calyx 6 mm wide and 3 mm deep overall, 5 lobes, each 3 mm wide and 1.5 mm deep, scalloped, margins entire, tips obtuse, glabrous, inside and outside Green 138B; stamen 10 in a ring around the pistil, each 7 mm long, 1 mm wide, filaments 4 mm long and 1 mm wide, Yellow Green 145B, anthers 3 mm long and less than 1 mm wide, Greyed Orange 164A, pollen — none seen; 1 pistil 11 mm long and 4 mm wide, ovary 2 mm long and 4 mm wide, Green 137A, style 8 mm long and 0.8 mm wide, Green 138B, stigma Green 137B.
*Fragrance*.—None.

Fruit (berry):
*Date of 50% maturity in Silverton, Oreg.*.—Jul. 15, 2013.
*Fruiting period*.—Mid to late season.
*Number of clusters per plant*.—About 38.
*Fruit cluster density*.—Medium.
*Berry size*.—Grow to 1.8 cm wide and 10 mm deep.
*Berry shape*.—Oblate spheroid, slightly flattened.
*Berry color*.—Closest to Violet Blue N92C without glaucous bloom, glaucous bloom Violet Blue 98D, flesh Greyed Green 192D.
*Fruit stem scar*.—Small, 1 mm.
*Berry firmness*.—Extremely firm.
*Berry flavor and texture*.—Medium sweet, floral.
*Berry calyx basin*.—Average 7 mm wide and 3 mm deep.
*Berry acidity*.—Medium.
*Fruit sweetness*.—Medium.
*Pollination requirement*.—Medium.
*Fruiting type*.—Fruits on one year old shoots.
*Storage quality*.—Excellent.
*Suitability for mechanical harvest*.—Excellent.
*Uses*.—Mechanical harvest, fresh market, home.

Seed:
*Seed abundance in fruit*.—Very low, 0 to 12 per fruit.
*Seed color*.—Greyed Orange 174A.
*Seed size*.—1.0 to 1.5 mm long.

Pest and disease tolerance: No exceptional disease or pest resistance or susceptibility observed. Typical for mid southern highbush blueberries.

I claim:

1. A new and distinct Northern Highbush blueberry plant as herein illustrated and described.

* * * * *